United States Patent
Padgett et al.

[11] Patent Number: 6,129,710
[45] Date of Patent: *Oct. 10, 2000

[54] NEEDLE CANNULA ATTACHMENT DEVICE FOR A DISPOSABLE SYRINGE

[75] Inventors: Mary Beth B. Padgett, Greensboro, N.C.; Quinton J. Farrar, Lakeville, Mass.

[73] Assignee: Spectrum Biotech Inc., Carson City, Nev.

[*] Notice: This patent issued on a continued prosecution application filed under 37 CFR 1.53(d), and is subject to the twenty year patent term provisions of 35 U.S.C. 154(a)(2).

[21] Appl. No.: 08/854,782

[22] Filed: May 12, 1997

[51] Int. Cl.7 ...................................................... A61M 5/32
[52] U.S. Cl. ........................................... 604/195; 604/110
[58] Field of Search ..................................... 604/110, 195, 604/228, 229, 239–243, 181, 187, 218, 221, 222, 263; 128/919

[56] References Cited

U.S. PATENT DOCUMENTS

| | | |
|---|---|---|
| 4,804,370 | 2/1989 | Haber et al. . |
| 4,808,169 | 2/1989 | Haber et al. . |
| 4,826,489 | 5/1989 | Haber et al. . |
| 4,838,870 | 6/1989 | Haber et al. ............................. 604/187 |
| 4,909,794 | 3/1990 | Haber et al. . |
| 4,931,040 | 6/1990 | Haber et al. . |
| 4,935,014 | 6/1990 | Haber . |
| 4,947,863 | 8/1990 | Haber et al. . |
| 5,026,355 | 6/1991 | Sweeney et al. . |
| 5,085,638 | 2/1992 | Farbstein et al. . |
| 5,092,853 | 3/1992 | Couvertier, II . |
| 5,112,307 | 5/1992 | Haber et al. . |
| 5,201,719 | 4/1993 | Collins et al. . |
| 5,342,309 | 8/1994 | Hausser .................................. 604/110 |
| 5,382,235 | 1/1995 | Sak ......................................... 604/110 |
| 5,403,288 | 4/1995 | Stanners . |
| 5,496,278 | 3/1996 | Buff ....................................... 604/195 |
| 5,501,670 | 3/1996 | Sak ........................................ 604/195 |
| 5,527,288 | 6/1996 | Gross et al. ............................ 604/145 |
| 5,538,507 | 7/1996 | De Kler et al. . |
| 5,558,651 | 9/1996 | Crawford et al. . |
| 5,569,203 | 10/1996 | Chen . |
| 5,653,698 | 8/1997 | Niedospial et al. .................... 604/283 |

Primary Examiner—Glenn K. Dawson
Assistant Examiner—Jeremy Thissell

[57] ABSTRACT

The present invention provides a safety syringe having a syringe cylinder, a piston stem, a needle cannula capable of being retracted into said syringe cylinder, and a needle cannula attachment hub capable of attachment to the syringe cylinder. An interior configuration of the hub includes a narrow distal portion and an enlarged well area disposed proximal thereto. The narrow distal portion may also include a plurality of annular grooves. The well area and the annular grooves are capable of being filled with an adhesive for attaching the hub to the needle cannula such that high forward needle pull-out forces and lower reverse needle pull-out forces are obtained.

20 Claims, 4 Drawing Sheets

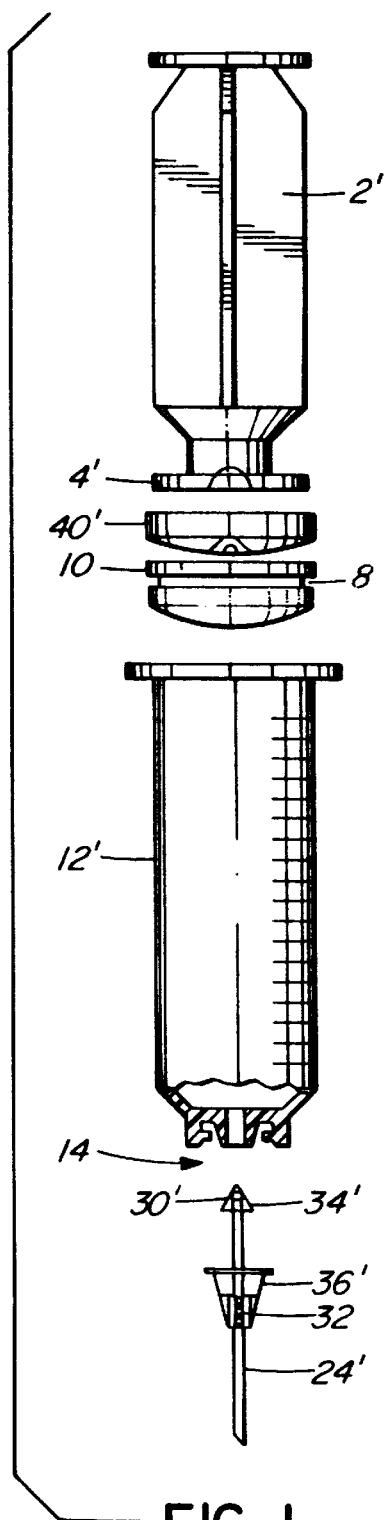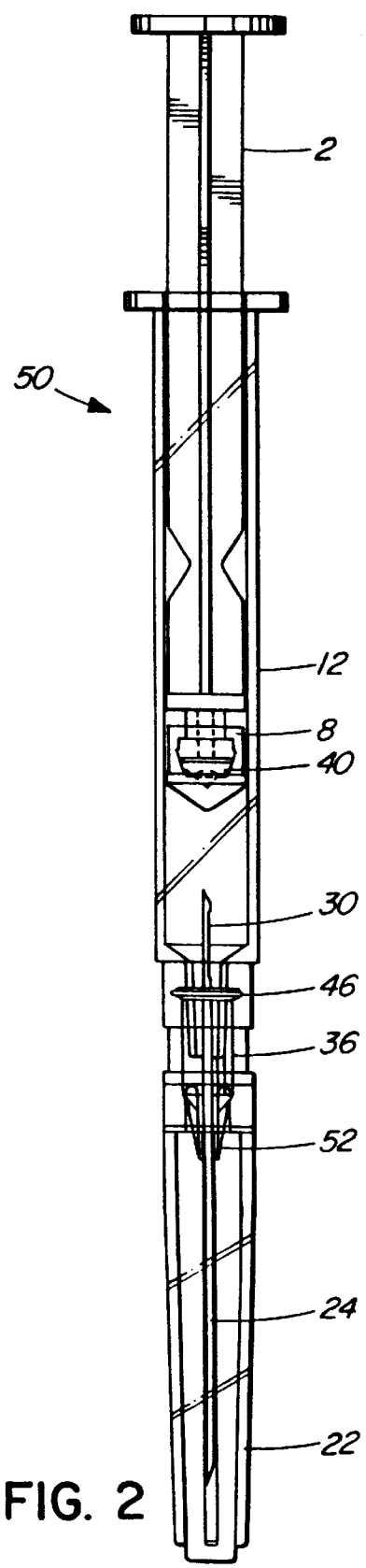
FIG. 1 PRIOR ART
FIG. 2

NEEDLE CANNULA ATTACHMENT DEVICE FOR A DISPOSABLE SYRINGE

TECHNICAL FIELD

The present invention is directed to a disposable safety syringe for injecting medication into a patient, and more particularly to a safety syringe including a retractable needle cannula and an improved method and device for receiving and capturing the same within the cylinder of the syringe after expulsion of the medicant.

BACKGROUND OF THE INVENTION

Disposable hypodermic syringes are routinely used to administer medication to patients, thus presenting the requirement for proper disposal of the used and contaminated needles. In an emergency situation, this requirement sometimes is overlooked by the health care technician, whether for practical reasons or otherwise. Separate procedures for disposal are limited at best, consisting of (i) breaking the needle off in a special container which is separate from the syringe, or (ii) using special equipment to assemble or disassemble the syringe, both of which require extra steps for proper disposal of the contaminated device.

Even needles which are broken off still can present a hazard of so-called "needle strikes" to trash removal personnel. The potential for needle strikes to health care technicians and associated personnel can cause a high degree of anxiety and require expensive testing procedures of suspected needle strikes. More and more health care personnel are exposed to the risk of infection with the increasing care requirements of HIV- and AIDS-infected individuals, as well as the risk of hepatitis B and other infectious diseases.

Prior attempts to address safe disposal of contaminated needles by retracting the used needle into the cylinder of the syringe are illustrated by, for example, U.S. Pat. No. 4,995,870 disclosing a structure which requires loosening of the hub in order to release the needle from a plug and thus allow for withdrawal of the used needle into the cylinder of the syringe. While manipulating the hub to allow for the retraction, the technician must either expose his/her hand to the distal end of the used and possibly contaminated needle or use an auxiliary device for covering the tip of the used needle.

The needles of U.S. Pat. Nos. 4,026,287, 4,804,370, and 5,221,262 all are integral with the syringe cylinder rather than being removably attachable assemblies and, thus, prevent adaptability to syringes having a so-called Luer lock connection or other types of removable attachments for non-integral needle assemblies.

Some prior art devices have so-called extended needles which protrude proximally into the syringe cylinder past their points of attachment to the needle assembly such that complete expulsion of fluid from a cylinder is negated. Since fluid is not compressible, any residual fluid in the distal end of the cylinder opposes further distal movement of the piston once the proximal opening of the needle is blocked by the piston or otherwise. Under this condition, further distal movement of the piston and capturing of the extended needle for retraction is rendered non-functional or, at best, difficult. Still other prior art devices provide for a barbed, proximal end of the extended needle to be impaled in a full (as opposed to hollow) piston or the like to effect capture and retraction, thus requiring more force to effect the capture.

The above-described needle receivers of the prior art are integral with the corresponding piston stems and, thus, do not present a structure which lends itself to retrofitting existing piston stems of syringes which are widely used in the industry. In contrast, however, in U.S. Pat. No. 5,382,235 to Sak (the '235 patent), the entire contents of which are hereby incorporated by reference, the needle cannula is modified and a deflector member and capturer are retrofit to the syringe in order to safely retract and capture the used needle cannula. As shown in FIG. 1, the '235 patent provides an elongated piston stem 2' of a typical syringe having a distal end flange 4' which is engageable within groove 10 of generally hollow rubber piston 8. A capturer 40' is receivable within the hollow portion of rubber piston 8 and retained therein by completion of the attachment of the piston 8 to the flange 4'. The typical syringe also includes a cylinder 12' to the distal end of which a separate needle assembly is removably attachable 14. The point of attachment typically is provided with a Luer lock-type of connection which is well known to those skilled in the art. The needle assembly is illustrated as comprising the cannula 24' which is modified to have at least one lateral port 30' and a conically shaped deflector member 34' attachable thereto in a generally permanent manner. Cannula 24' also has grooves 32 to aid in attachment of the Luer lock-type hub 36' onto the cannula 24' by means of an adhesive. The distal end of cannula 24' is pointed for insertion into the patient and the proximal end thereof is sharpened for piercing of the rubber piston 8 upon complete expulsion of the fluid contained in cylinder 12'. In order to ensure uninterrupted and complete expulsion of fluid from cylinder 12', the so-called extended needle cannula 24' is provided with one or more of the lateral ports 30' for evacuation of any fluid remaining upon the proximal end of cannula 24'. Although retrofittable to existing syringes, the invention of the '235 patent discloses modification of the needle cannula such as annular grooves 32' and the manufacture of additional components such as deflector 34', all of which increase the cost of producing the device for capturing and receiving the needle cannula of the syringe.

BRIEF SUMMARY OF THE INVENTION

The present invention overcomes the disadvantages of the prior art while still obtaining the advantages thereof by providing a needle cannula attachment hub capable of attachment to a syringe cylinder, wherein an interior configuration of the hub includes a narrow distal needle securing portion and an enlarged well area disposed proximal thereto. The narrow distal portion preferably also includes at least one annular groove. The well area and any annular groove is filled with an adhesive for attaching the hub to the needle cannula. Having adhesive in the well area necessitates a significant force being used to pull the needle in a forward direction, and thereby substantially prevents forward pull, yet the adhesive in the annular groove necessitates a lesser force being used to pull the needle in a reverse direction. The adhesive used is also preferably compressible such that, upon reverse pull of the needle, the adhesive in the annular groove attaching the needle to the hub means is compressed and pulled away from the groove substantially intact. Thus, the mass of adhesive will remain substantially intact and adhere to the needle cannula when it is retracted into the syringe cylinder.

Various additional advantages and features of novelty which characterize the invention are further pointed out in the claims that follow. However, for a better understanding of the invention and its advantages, reference should be made to the accompanying drawings and descriptive matter which illustrate and describe preferred embodiments of the invention.

BRIEF DESCRIPTION OF THE DRAWINGS

FIG. 1 is an exploded view, partially in cross-section, of a disposable syringe modified by incorporation of the invention of the '235 patent;

FIG. 2 is an elevational view of the syringe assembly according to a preferred embodiment of the present invention;

DETAILED DESCRIPTION OF THE INVENTION

Figure 3:
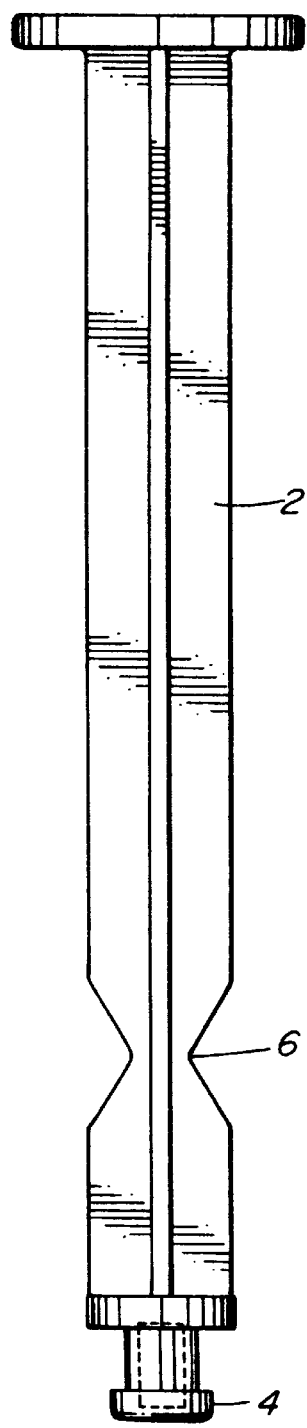
FIG. 3 is an elevational view of a piston stem of the syringe assembly of FIG. 2.

Referring to FIG. 2, a syringe assembly according to a preferred embodiment of the present invention is shown generally by reference numeral 50. Syringe assembly 50 includes a piston stem 2, a cylinder 12 onto which a Luer lock-type hub 36 is secured, a needle cannula 24, and a capturing device 40, each of which is explained in greater detail below.

Referring to FIG. 3, piston stem 2 is shown generally by the figure. The elongated piston stem 2 includes distal end flange 4 that is engageable within groove 10 of generally hollow rubber piston 8. The piston 8 includes a reduced thickness notch portion 6 in order to permit the bulk of the piston stem to be broken away from the proximal end after use and the stem has been retracted from the cylinder 12. A hole may be provided in the distal end of the piston stem to allow extended needle cannula to telescope into the plunger whereby the side port in the cannula may come into engagement with the capturing device.

Figure 5:
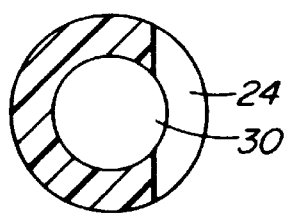
FIG. 5 is a cross-sectional view taken along the line 5—5 of FIG. 4.
Figure 4:
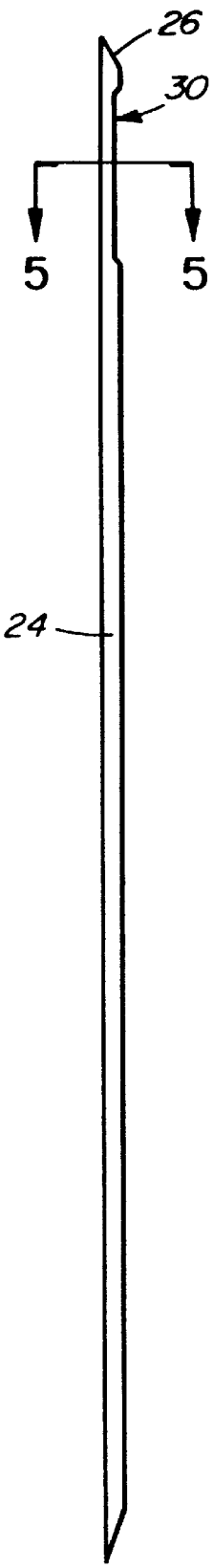
FIG. 4 is an elevational view of a needle cannula of the syringe assembly of FIG. 2.

FIGS. 4 and 5 illustrate a stainless steel needle cannula 24 according to the present invention and having at least one lateral port 30. The distal end of cannula 24 is pointed for insertion into the patient and the proximal end 26 may be beveled for piercing of the rubber piston 8 upon complete expulsion of the fluid contained in cylinder 12. In order to ensure uninterrupted and complete expulsion of fluid from cylinder 12, the so-called extended needle cannula 24 is provided with one or more of the lateral ports 30 for evacuation of any fluid remaining upon the proximal end 26 of cannula 24 becoming blocked by the piston 8 or associated structure at the distal end of stem 2. In a preferred embodiment of the present invention, cannula 24 is a twenty-two gage needle with the length of the cannula, including proximal end 26, having a diameter of approximately 0.028". The lateral port 30 defines a reduced cannula circumference and defines a height of approximately 0.020" at the location thereof.

Figure 6:
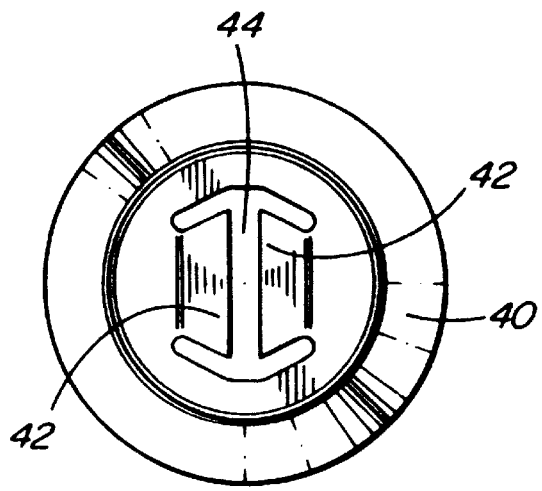
FIG. 6 is a plan view of a capturing device of the syringe assembly of FIG. 2.
Figure 7:
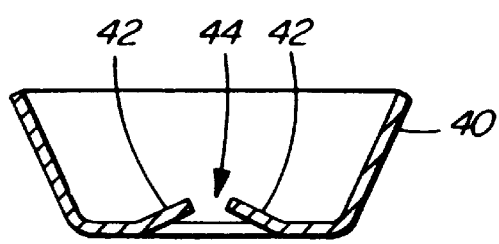
FIG. 7 is a side elevational view of the capturing device of FIG. 6.
Figure 8:
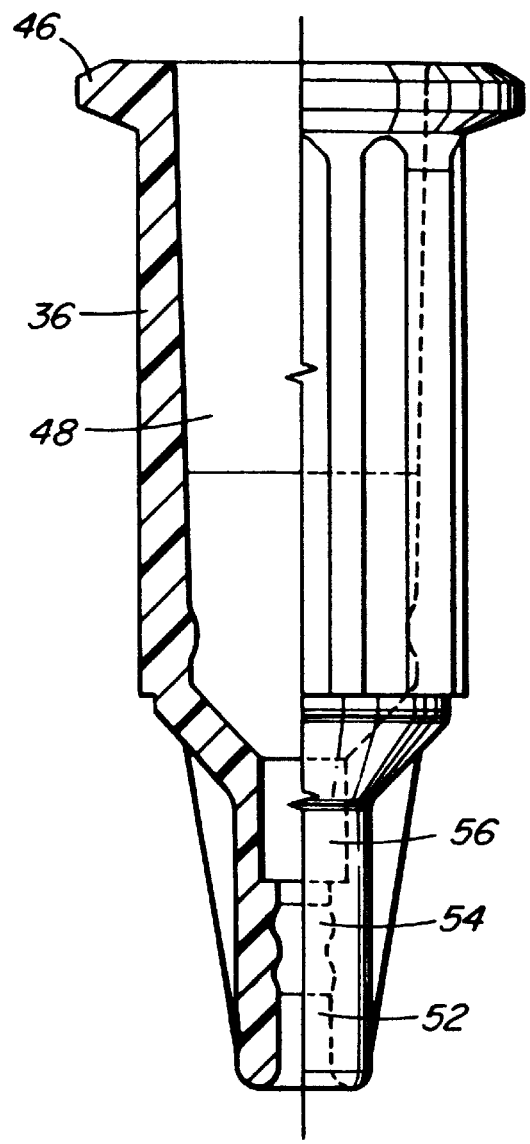
FIG. 8 is a side elevational view of a hub of the syringe assembly of FIG. 2 in partial cross section.
Figure 9:
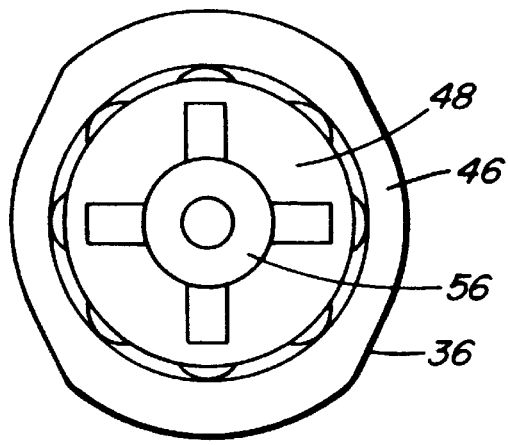
FIG. 9 is an end elevational view of the hub of FIG. 8.
Figure 11:
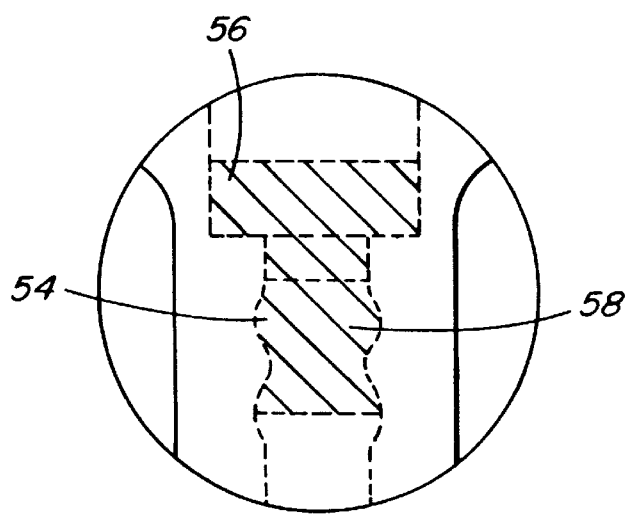
FIG. 11 is an enlarged detail of a portion of the hub as shown in FIG. 10.
Figure 10:
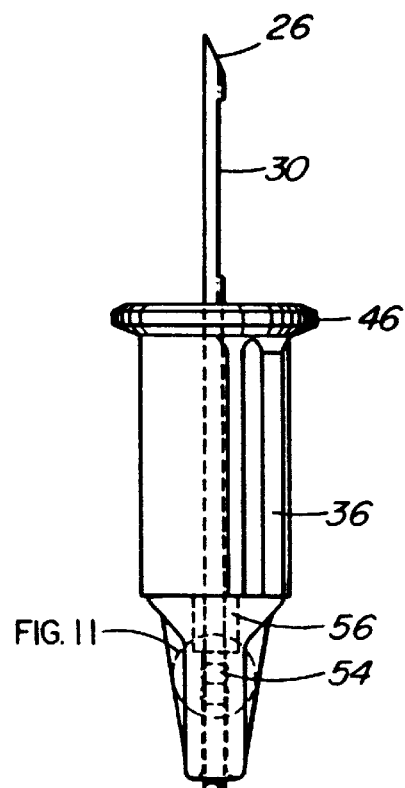
FIG. 10 is an assembled view of the hub of FIG. 8 and the needle cannula of FIG. 4.

FIGS. 6 and 7 illustrate a capturing device 40 having flexible tabs 42 for capturing the needle cannula 24 therein in order to effect subsequent retraction of the needle into cylinder 12. The opposing edges of the tabs 42 define a longitudinal opening 44 of approximately 0.021". The capturing device 40 is installed within the concavity of piston 8 and retained securely therein by mating flange 4 of the typical stem 2 in piston groove 10. Thus, after piercing the rubber piston 8, the tabs 42 bend as the larger diameter proximal end passes through opening 44. Then, when the smaller lateral port 30 is within the opening 44, the tabs 42 bend back to their original location and essentially lock around the port 30 to thereby prevent forward and reverse pull of the needle cannula out of the capturing device.

Referring to FIGS. 8–11, the Luer lock-type hub 36 according to the present invention is shown in greater detail. The hub is molded polypropylene but other polymer products having the same characteristics are contemplated. Hub 36 includes a proximal flange 46 for engagement with the conventional threaded distal end of cylinder 12, a barrel portion 48, and a straight needle securing portion 52. Needle securing portion 52 includes one or a plurality of internal grooves 54 and an enlarged well area 56 disposed proximally thereto. An adhesive 58 is preferably disposed within the internal grooves 54 and well area 56, as shown by cross-hatched area of FIG. 11. When the grooves 54 and well 56 are filled with the correct amount of a suitable adhesive, as discussed in detail below, in the correct location, the preferred needle pull-out forces are obtained. That is, contrary to prior art syringes having high cannula pull-out forces in both the forward and reverse directions, the present invention obtains high forward cannula pull-out forces by placing the adhesive in the well 56, however, lower reverse cannula pull-out forces are obtained by placing adhesive in the annular grooves 54 in the needle securing portion 52 of the hub 36. When needle cannula 24 is pulled from the hub 36 the adhesive used to secure the cannula thereto stays intact and attached to the cannula 24, the adhesive chosen adhering to stainless steel but have poor adhesion to the polypropylene hub. Accordingly, forward pull of needle cannula from hub 36 is substantially prevented by the well 56 of adhesive securely holding needle cannula 24 since a high force would be required to overcome the well of adhesive and to compress the adhesive such that it passes through the narrower annular grooves 54 and is removed with the cannula. On the other hand, reverse pull of needle cannula must only overcome the short area of interference fit as the adhesive within the grooves passes through the narrower groove restrictions in order for the needle cannula with the adhesive attached thereto to be pulled out. Accordingly, the lower reverse pull-out forces are necessary in order to obtain a smooth release of the needle cannula 24 from the hub 36 when the needle is captured by the capturing device 40.

Prior art adhesives used for securing a needle cannula to a hub have generally included heat cured epoxies. Such adhesives are brittle, and if used with the hub 36 of the present invention, a rear pull-out force applied thereto would likely cause the adhesive to shear off and/or flake, thereby adding contaminants to the needle assembly. Accordingly, a preferred adhesive to be used with the hub 36 of the present invention must be slightly flexible so that it may be compressed during rearward pull-out of the needle cannula and thereby adhere in entirety to the needle cannula. Urethane acrylate is a preferred suitable adhesive due to its flexibility, and in particular an adhesive known as ULTRA-LIGHT-WELD™ 1-20271 cannula bonder that is produced by Dymax Corporation of Torrington, Conn. Other adhesives produced by Loctite, such as numbers 3102, 3103 and 322, may work equally as well with needle assembly 50, especially number 3102 due to the similarity in viscosity and tensile shear strength. The preferred tensile break strength of the adhesive should be approximately 3300 pounds per square inch with an elongation of approximately 60% at break. The adhesive preferably is non-migratory having a high viscosity, preferably approximately 4000 centipoise or greater, so that it is self-maintained in the area of the needle cannula when it is applied thereto. Lower viscosity adhesives that are typically used in prior art syringes tend to wick down the needle such that the final location of the adhesive is difficult to control. The preferred Dymax adhesive has a viscosity of 4000 cp whereas the Loctite 3102 adhesive has a viscosity of 3750 cp. Similarly, the preferred Dymax adhesive has a tensile shear strength of 3000 psi with a 90% elongation at break whereas the Loctite 3102 adhesive has a tensile shear strength of 2500 psi. Other adhesives having other viscosity values, tensile strength values, and elongation values may of course also be used provided that the objects of the present invention are still achieved. That is, the adhesive must adhere substantially where it is applied to the needle cannula 24 and the adhesive must be sufficiently flexible such that it will compress and stay substantially intact and adhered to the needle cannula 24 when the cannula is pulled out in the reverse direction from the hub 36.

In use of the invention, the receiving device 40 is installed within the concavity of piston 8 and retained securely therein by mating flange 4 of the stem 2 in piston groove 10 during packaging of the syringe. The packaged syringe has stem 2 at least partially telescoped into cylinder 12. A needle assembly including hub 36 and needle cannula 24 may be pre-assembled or would be packaged with the standard sterility shield 22 for safe handling of the needle assembly during attachment thereof to the distal end of cylinder 12. Once the needle assembly is positioned on the syringe, the protection shield 22 is removed from the cannula 24 for infusing a fluid medicament into the cylinder 12. Upon complete expulsion of the medicament therefrom, the pointed proximal end 26 of the cannula 24 will pierce the rubber of piston 8 and pass between the flexible tabs 42 to effect capture of the needle cannula 24 within capturing device 40 as described above and telescope into the piston stem. A subsequent rearward force applied to piston stem 2 overcomes the adhesive force adhering the needle to hub 36 such that needle cannula 24 may be retracted and the adhesive is pulled free from the walls of the needle securing portion 52 of the hub 36. The contact of the hole 30 with the tabs 42 permits the cannula to cant to one side when the needle is fully retracted inside the cylinder. Upon full retraction of piston stem 2, the used needle cannula 24 is safely disposed within the cylinder 12 for appropriate disposal and there is no danger of infection to the health care technician. The piston stem is then snapped off at the break-away notch and disposed of. This prevents the piston stem from being easily pulled out of the barrel with the needle still attached. It also prevents forward pressure being applied to the piston stem, causing the retracted needle to be pushed forward also and possibly puncturing through the wall of the syringe barrel.

In order to ensure that the adhesive is properly applied in the correct location, the preferred method of applying the adhesive and fixing the needle cannula 24 to the hub 36 is described below. A rack capable of holding one or a plurality of hubs is first horizontally positioned on a table top. The hub rack is designed to locate the cannula in the correct location relative to the hub and to minimize angularity of the cannula in the hub. Hubs are loaded onto the hub rack and slid down onto the hub rack face. The needle cannula 24 is slid into the hub 36 through the distal end thereof, the proximal end 26 of the needle being inserted first. The hub is then slid forward toward the distal end of the needle, being careful not to damage the point of the needle. An automatic adhesive dispensing system is adjusted and fixtured so that the correct drop size (approximately 0.020 cc) of adhesive is dispensed onto the cannula at the proper location as measured from the proximal end of the cannula. The hub is slid proximally along the needle and moved into place seated on the hub rack face. The hub should be moved axially along the needle and not twisted or rotated during the sliding process. The hub rack is then moved to an apparatus for ultra-violet light curing of the adhesive. A conveyor system with a fusion ultra-violet light curing system is preferably used, such as the UVC conveyor cure system UVC-6 of Dymax Corporation of Torrington, Conn. utilizing Dymax's 5000-EC UV/Visible flood lamps. After curing, the proximal end of the needle cannula may be lightly pulled to check for any looseness and to confirm proper curing of the adhesive and the entire assembly should be visually inspected to ensure that there is no excess adhesive.

Thus, it will be seen that the objects set forth above, among those made apparent from the preceding description, are efficiently attained and, since certain changes may be made in the construction set forth without departing from the scope of the invention, it is intended that all matter contained in the above description or shown in the accompanying drawings shall be interpreted as illustrative and not in a limiting sense. For instance, although the invention has been described with respect to removably attachable needle assemblies, it is also contemplated that similar adaptations may be made to those needle assemblies which are affixed to be integral with the syringe.

It is to be understood also that the following claims are intended to cover all of the generic and specific features of the invention herein described, and all statements of the scope of the invention which, as a matter of language, might be said to fall therebetween.

We claim:

1. A safety syringe comprising:
a syringe cylinder and a needle cannula capable of being retracted into said syringe cylinder; and
a plunger assembly movable in said syringe cylinder, said assembly comprising:
a piston stem;
a piston mountable on a distal end of said piston stem, said piston having a void formed therein; and
a needle capture member received within said void, said needle capture member being arranged such that, in use, a proximal end of the needle cannula is passed through and secured within the capture member at the end of an injection stroke; and
a needle cannula attachment hub capable of attachment to said syringe cylinder, said hub attaching said needle cannula to said syringe such that said needle cannula is retractable into said syringe cylinder, said hub comprising a passageway through said hub with said needle cannula received therein, said passageway comprising:
an adhesive well area and adhesive received therein to releasably attach said needle cannula to said hub such that said needle cannula and said adhesive are pulled away from said hub upon retraction of said needle cannula; and
a narrow distal portion having at least one annular groove and adhesive received therein to further releasably attach said needle cannula to said hub, and;

said adhesive well area being disposed proximal to said narrow distal portion, said well area having a larger diameter than said narrow distal portion;

wherein said adhesive in said adhesive well area necessitates a significant force being used to pull said needle in a distal direction and said adhesive in said at least one annular groove necessitates a lesser force being used to pull said needle in a proximal direction.

2. A safety syringe according to claim 1, wherein said needle capture member includes at least one flexible tab for flexing toward an open state in a proximal direction during entry of said needle into said needle capture member and back toward a closed state to effect capturing of said needle.

3. A safety syringe according to claim 2, wherein said needle includes at least one lateral aperture on a proximal end thereof providing for fluid passage laterally from an axial bore of said needle, said aperture being engageable with said tab to thereby capture said needle.

4. A safety syringe according to claim 1, wherein said piston stem includes a concavity on a distal end thereof for allowing sufficient room for the proximal end of the said needle after said needle is captured by said needle capture member.

5. A safety syringe according to claim 1, wherein said piston stem has a flange at a distal end thereof and said piston presents a concavity facing proximally of said syringe and a groove in an internal surface of said concavity, said groove being engageable by said flange to facilitate attachment of said piston to said stem while leaving said void generally defined by said stem distal end and said internal surface of said concavity.

6. A safety syringe according to claim 1, wherein the adhesive provides a stronger bond to metal material as compared to plastic and polypropylene material.

7. A needle cannula and hub assembly comprising:
(a) a hub having:
   (i) a syringe attachment end attachable to a syringe;
   (ii) a distal end opposite said syringe attachment end;
   (iii) a passageway through the hub, said passageway comprising a well and a narrow passage connecting the well and the distal end, the well having a larger cross-sectional area than the narrow passage;
(b) a needle cannula having a portion extending through said passageway and a portion extending outside the hub beyond the syringe attachment end; and
(c) adhesive adhered to the needle cannula in the well and in sufficient amount to cooperate with said well to necessitate a greater force to move the needle cannula in a direction towards the distal end than in a direction towards the syringe attachment end.

8. The assembly of claim 7 wherein adhesive is adhered to the needle cannula in the narrow passage.

9. The assembly of claim 8 wherein the narrow passage includes one or more annular grooves.

10. The assembly of claim 9 wherein the adhesive adhered to the needle cannula in the narrow passage is compressible and is received in said one or more annular grooves.

11. The assembly of claim 10 wherein said compressible adhesive is a flexible urethane acrylate.

12. The assembly of claim 8 wherein the adhesive adhered to the needle cannula in the well and in the narrow passage is a flexible urethane acrylate.

13. The assembly of claim 12 wherein the needle cannula is comprised of stainless steel, and the hub is comprised of polypropylene.

14. The assembly of claim 7 wherein said adhesive has greater adhesion to the needle cannula than to the well.

15. The assembly of claim 14 wherein the portion of the needle cannula extending through the passageway is of substantially constant diameter.

16. A needle cannula and syringe assembly comprising:
(a) a syringe with a hub for holding a needle cannula, the hub comprising:
   (i) a first end connected to said syringe;
   (ii) a second end opposite said first end;
   (iii) a passageway through the hub, said passageway comprising a well and a narrow passage connecting the well and the second end, the well having a larger cross-sectional area than the narrow passage;
(b) a needle cannula having a portion extending through said passageway and a portion extending into said syringe; and
(c) adhesive adhered to the needle cannula in the well and in sufficient amount to cooperate with said well to necessitate a greater force to move the needle cannula in a direction towards the distal end than in a direction towards the syringe.

17. The assembly of claim 16 wherein adhesive is adhered to the needle cannula in the narrow passage.

18. The assembly of claim 17 wherein the adhesive adhered to the needle cannula in the well and in the narrow passage has greater adhesion to the needle cannula than to the hub.

19. The assembly of claim 18 where the portion of the needle cannula extending through the passageway is of substantially constant diameter.

20. The assembly of claim 16 wherein said syringe comprises a piston including a needle capture member capable of cooperating with said portion of the needle cannula extending into the syringe, for retraction of the needle cannula.

* * * * *